United States Patent [19]

Haughton

[11] Patent Number: 5,222,965
[45] Date of Patent: Jun. 29, 1993

[54] TEAT KNIFE

[76] Inventor: Donald Haughton, R.D. #1, Box 33, Little Falls, N.Y. 13365

[21] Appl. No.: 755,663

[22] Filed: Sep. 6, 1991

[51] Int. Cl.$^5$ .......................................... A61B 10/00
[52] U.S. Cl. ..................................... 606/159; 606/167
[58] Field of Search ............... 606/159, 167, 191; 128/751; 604/22, 274, 180; 30/29.5, 240

[56] References Cited

U.S. PATENT DOCUMENTS

| | | | |
|---|---|---|---|
| 68,647 | 9/1867 | Palmer | 606/159 |
| 737,293 | 8/1903 | Summerfeldt | 606/159 |
| 1,625,906 | 4/1927 | Naylor | 606/191 |
| 1,663,761 | 3/1928 | Johnson | 606/159 |
| 1,837,503 | 12/1931 | Thostenson | 606/159 |
| 2,676,595 | 4/1954 | Dyekjaer | 606/159 |
| 2,730,101 | 1/1956 | Hoffman | 606/159 |
| 2,816,551 | 12/1957 | Hoffman | 606/159 |
| 3,336,927 | 8/1967 | Klebanoff | 606/159 |
| 4,986,807 | 7/1991 | Farr | 606/159 |
| 5,007,917 | 4/1991 | Evans | 606/170 |
| 5,019,088 | 5/1991 | Farr | 606/159 |

FOREIGN PATENT DOCUMENTS

| | | | |
|---|---|---|---|
| 36537 | 9/1926 | Denmark | 606/159 |
| 808082 | 3/1981 | U.S.S.R. | 606/159 |
| 1150232 | 3/1969 | United Kingdom | 606/159 |

Primary Examiner—Edgar S. Burr
Assistant Examiner—Anthony H. Nguyen
Attorney, Agent, or Firm—Wall and Roehrig

[57] ABSTRACT

A simplified unitary teat knife is formed of stainless steel rod with a knurled knob on one end and an eye on the other. The eye is flattened and enlarged relative to the rod of the knife and the edges of the eye are sharpened so as to provide cutting surfaces for removal of obstructions within the milk duct as the tool is rotated within the duct by manual manipulation of the knurled knob.

3 Claims, 1 Drawing Sheet

TEAT KNIFE

BACKGROUND OF THE INVENTION

This invention relates to an instrument for removing unwanted obstructions in the milk duct of a cow teat which hinder or stop the flow of milk therethrough. More particularly, this invention is directed toward a simplified unitary knife structure for safely and thoroughly removing scar tissues, small floating cysts, tumors and the like from the interior of the milk duct of a cow's teat.

In the dairy industry, it is not uncommon to encounter difficulty in obtaining milk from one or more teats of a particular cow. This is usually caused by an obstruction of scar tissue, membrane cartilage or other growth within the milk duct of the teat and severely curtails the milk production from the cow. Various devices have been proposed over the years for clearing the duct of the teat from these obstructions, with most of them being of the curette type for actually severing a growth from the lining of the milk duct to various multiple acting instruments for removing growths which have required manipulation of at least two elements requiring generally the use of two hands to affect the desired clearing of the milk duct. U.S. Pat. Nos. 1,837,503; 1,663,761; and 737,293 are typical of this type of apparatus where a hollow shaft has an aperture forming a cutting surface in the distal end and a rod positioned in the shaft interior has a cooperating surface for severing a protrusion captured by said aperture. The manipulation of the interior and the exterior actuating members usually requires two hands. Another approach has been that of U.S. Pat. No. 2,816,552 in which a set of knives is expanded by an internal threaded rod which expands flexible blades to an enlarged diameter so that the interior of the milk duct can be scrapped to enlarge same and remove undesired obstruction. Various veterinary knives have been proposed which can be manipulated to remove tissue from the interior of the milk duct of the teat and these are represented by U.S. Pat. No. 2,676,595.

All of these prior art devices have been difficult to use or have required the expert services of a veterinarian to properly remove the obstruction without injuring the teat of the cow. While some of these devices have permitted removal of the obstruction, they have frequently caused additional injury to the teat and ultimately resulted in lack of milk flow, resulting in premature termination of the milking life of the cow.

OBJECTS AND SUMMARY OF THE INVENTION

It is accordingly an object of the present invention to provide an improved teat knife that overcomes the limitations of the prior art.

It is another object of the present invention to provide a simplified teat knife that can be easily and readily used by dairy farmers and veterinarians alike.

It is another object of the present invention to provide a simplified, unitary construction of a teat knife that can remove obstructions, but will not accidentally gouge or otherwise damage the interior lining of the milk duct of the cow's teat.

It is another object of the present invention to provide a teat knife in the form of a rod having a needle's eye in the distal end with at least one edge sharpened for removal of obstructions upon insertion and rotation within the milk duct of the teat.

It is another object of the present invention to provide a teat knife of simplified construction such that it can be made from stainless steel or other suitable materials that can be easily and simply cleaned and sterilized.

These and other and further objects and advantages of the present invention are obtained in a preferred embodiment by a narrow stainless steel rod having a knurled knob on one end for rotation thereof and having a flattened eye portion at the other end in which a slot is formed and at least one edge of the slot is sharpened to provide a knife action within the milk duct of the teat as the knife assembly is rotated by rotating the knob at the proximal end of the teat knife. The sharpened edge of the eye formed in the distal end of the teat knife not only cuts the obstruction loose, but it also helps to capture the obstruction and to permit freeing it from the wall of the milk duct as well as removal of the severed tissue.

BRIEF DESCRIPTION OF THE DRAWINGS

For a better understanding of these and other objects of the present invention, reference is made to the detailed description of the invention which is to be read in conjunction with the following drawings, wherein.

DETAILED DESCRIPTION OF A PREFERRED EMBODIMENT

Figure 1:
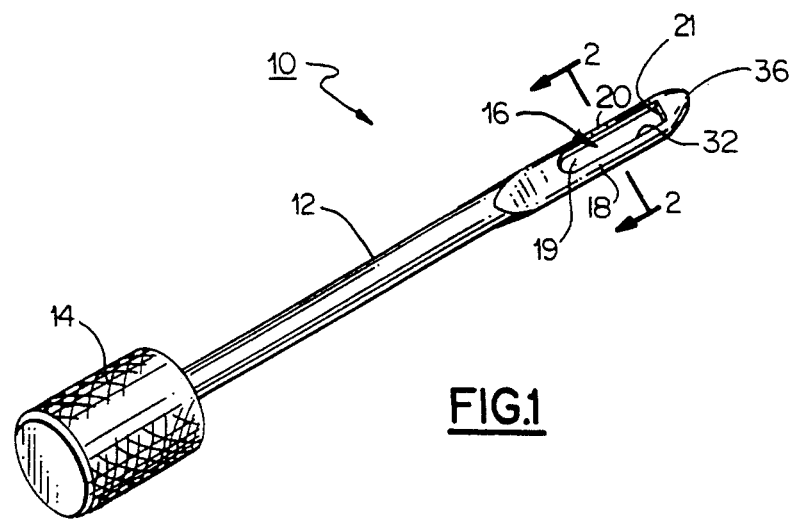
FIG. 1 is a perspective view of one embodiment of a teat knife according to the present invention.

Referring now to FIG. 1, there is shown a teat knife 10 in accordance with the present invention. The body of the teat knife is formed by an elongated narrow cylindrical rod 12 which has an enlarged knurled knob 14 at one end and an enlarged flattened eye area 16 at the other end. The instrument is formed as an integral unitary piece and is designed to be operated by the fingers of one hand manipulating the knurled knob 14 in a rotary fashion after inserting the rod 12 inside the milk duct of the teat of the cow. The farmer, in normal use, will insert the knife in the teat while holding the teat in the other hand and rotate the eye knife portion so as to remove the obstruction limiting the flow of milk through the milk duct.

Figures 2, 3:
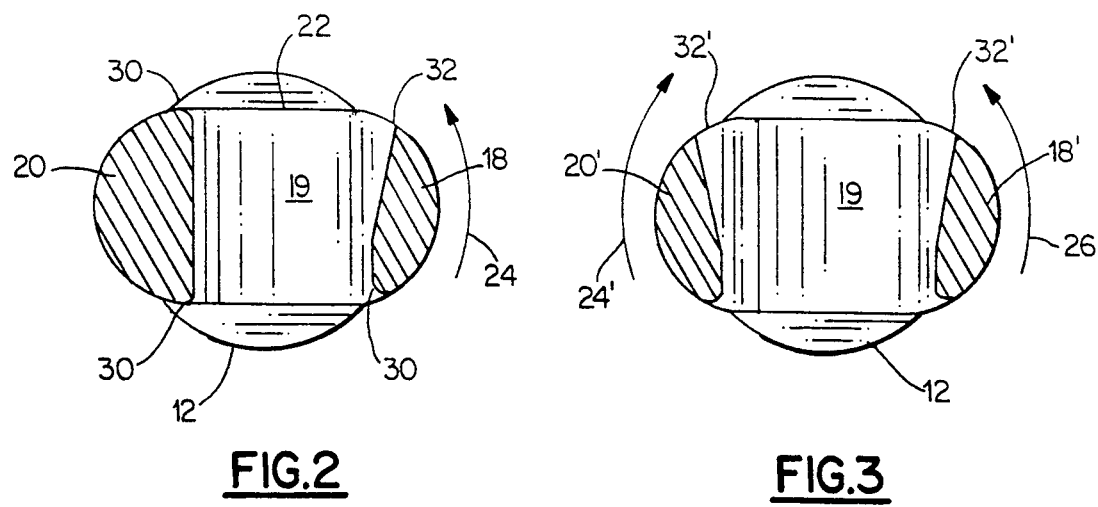
FIG. 2 is a cross-section taken on line 2—2 of FIG. 1.
FIG. 3 is a view similar to FIG. 2 of another embodiment of the present invention.

Referring to FIG. 2 there is shown an enlarged cross section of the eye portion 16 of the knife 10. As may be seen, the eye portion 16 is enlarged in width compared to the diameter of the rod 12, to the dimension shown relatively in FIG. 2. The width of the eye portion 16 is approximately fifty percent greater than the diameter of the rod portion 12. The eye portion 16 is somewhat flattened and has two side members 18 and 20 disposed on either side of a slot 19. The outer surfaces of 18 and 20 are arcuate forming a portion of the circumference of a circle having a diameter approximately equal to the width of eye portion 16. The two side members 18 and 20, in cross section, may be said to form approximate chordal segments of a circle drawn about the edges of the eye portion 16. As can be seen in FIG. 2, the side member 18 has a rounded edge 30 and a cutting edge 32, while the side member 20 has a rounded edge 30 on each edge thereof. The rounded edges are contoured so as to facilitate rotation of the knife 10 within the milk duct and the increased width of eye portion 16 with the rounded edges tends to guide or position the cutter in operative position with the inside surface of the milk duct. As also can be seen in FIG. 2, the cutting edge 32 is formed by sharpening the edge of the side member 18 from the inside out to form a cutter edge at the circumference of the eye portion 16. A rounded tip 36 is shown on the distal end of the eye to facilitate entrance of the knife into the milk duct and to help guide the tool into proper position within the milk duct.

During use, the enlarged cross section of the eye portion 16 and the rounded circumference of portions 18 and 20 serve to extend and support the duct so that an obstruction can be "captured" in the slot 19 of eye portion 16 and cut loose by rotation of cutter edge 32 for removal from the duct. The relative small size and rounded outer surfaces permit the tool to be used while inflicting minimum injury to the milk duct and teat of the cow.

Referring now to FIG. 3, there is shown another embodiment of the present invention in which the lower edge of each side member 18' and 20' is sharpened 32' in the manner shown in FIG. 2 to provide two sharpened cutters so that the tool will cut whether it is rotated in the clockwise or counter-clockwise direction.

In use, the tool is inserted into the obstructed milk duct of the teat with one hand while the obstruction is located with the other hand. The knife is positioned so that the eye 16 contacts or surrounds the obstruction. By rotating the knife as shown in FIG. 2 in the clockwise direction, the cutter edge 32 can be brought into contact with the obstruction and the obstruction cut or scraped from the lining of the milk duct. In the configuration shown in FIG. 3, the tool can be rotated in either the clockwise or counter-clockwise direction, whichever is more appropriate to sever and remove the obstruction from the lining of the milk duct of the teat.

For certain types of obstructions such as small "floating cysts", the distal end surface 21 of slot 19 of eye portion 16 has a width sufficient to capture the floating cyst in the eye and remove it from the milk duct by withdrawal of the knife from the teat. This distal surface 21 is disposed perpendicularly to the axis of rod 12.

It will thus be seen that I have provided a very simple tool easily and cheaply manufactured that can be effectively used to remove obstructions from the milk duct of the teat of a cow without causing serious injury to the cow. The tool being made of stainless steel is easily cleaned and sterilized.

While this invention has been explained with reference to the structure disclosed herein, it is not confined to the details set forth and this application is intended to cover any modifications and changes as may come within the scope of the following claims:

What is claimed is:

1. A teat knife for removing scar tissue, cysts and tumors that protrude from the interior wall of a teat milk duct that includes:

an elongated rod of given diameter having a longitudinal axis, a manipulating knob at its proximal end and an eye portion integral with the rod at its distal end being centered upon said longitudinal axis;

said eye portion having opposed flat top and bottom surfaces, the dimension across said top and bottom surfaces being less than the diameter of the rod and two opposed arcuate-shaped side surfaces, the maximum dimension between said side surfaces when viewed in a cross section perpendicular to said longitudinal axis being greater than the diameter of said rod;

an elongated opening formed in said eye portion that is centered along the longitudinal axis of said rod, said opening having opposed longitudinally extended side walls passing through the top and bottom surfaces of the eye portion to establish two rigid side members on either side of said opening; and a cutting edge formed between at least one side wall of the opening and the outer surface of one of said rigid members, whereby the rigid side members of the eye portion laterally extend the interior wall of the milk duct and scar tissue, cysts, tumors and the like protruding from the interior wall pass into the elongated opening of the eye portion and are cut away by said cutting edge as the rod is rotated.

2. The teat knife according to claim 1 including a second cutting edge formed between the opposed side walls and the outer surface of said rigid members.

3. The teat knife according to claim 1 wherein said eye portion has a rounded tip to facilitate entry into the teat milk duct.

* * * * *